United States Patent [19]

Ostreicher et al.

[11] 4,305,782

[45] Dec. 15, 1981

[54] FILTER AND METHOD OF MAKING SAME

[75] Inventors: Eugene A. Ostreicher, Farmington; Kenneth C. Hou, Glastonbury, both of Conn.

[73] Assignee: AMF Incorporated, White Plains, N.Y.

[21] Appl. No.: 147,975

[22] Filed: May 8, 1980

Related U.S. Application Data

[63] Continuation-in-part of Ser. No. 27,568, Apr. 6, 1979, abandoned.

[30] Foreign Application Priority Data

Nov. 16, 1979 [GB] United Kingdom ............... 39787/79

[51] Int. Cl.$^3$ .............................................. D21H 3/78
[52] U.S. Cl. ............................... 162/181 C; 210/503; 210/505
[58] Field of Search ............ 162/141, 164 EP, 181 R, 162/181 C, 187, 176, 183, 145; 210/503–505; 106/286.1; 55/528

[56] References Cited

U.S. PATENT DOCUMENTS

| | | | |
|---|---|---|---|
| 2,955,067 | 10/1960 | McBurney et al. | 210/505 |
| 3,007,878 | 11/1961 | Alexander et al. | 106/286.1 |
| 3,034,981 | 5/1962 | Poelman et al. | 162/145 |
| 3,242,073 | 3/1966 | Guebert et al. | 210/504 |
| 3,573,158 | 3/1971 | Pall et al. | 162/146 |
| 4,007,113 | 2/1977 | Ostreicher | 210/504 |
| 4,007,114 | 2/1977 | Ostreicher | 210/504 |

*Primary Examiner*—Peter Chin
*Attorney, Agent, or Firm*—George W. Price; Michael Zall

[57] ABSTRACT

A filter media sheet comprising fine particulate and a self-bonding matrix of cellulose fiber, the surfaces of at least one of which are modified with cationic colloidal silica.

14 Claims, 3 Drawing Figures

FILTER AND METHOD OF MAKING SAME

This is a continuation-in-part application of U.S. Ser. No. 027,568, filed Apr. 6, 1979, abandoned.

BACKGROUND OF THE INVENTION

This invention relates to filtration and, more particularly, to the removal of submicron contaminants from aqueous systems, utilizing filter media sheet comprising high levels of particulate filter aids.

The filtration of fine particle size contaminants from fluids has been accomplished by the use of various porous filter media through which the contaminated fluid is passed. To function as a filter, the media must allow the fluid, commonly water, through, while holding back the particulate contaminant. This holding back of the contaminant is accomplished by virtue of the operation, within the porous media, of one or both of two distinctly different filtration mechanisms, namely (1) mechanical straining and (2) electrokinetic particle capture. In mechanical straining, a particle is removed by physical entrapment when it attempts to pass through a pore smaller than itself. In the case of the electrokinetic capture mechanisms, the particle collides with a surface face within the porous filter media and is retained on the surface by short range attractive forces.

With the exception of microporous polymeric membranes, the porous filter media known to the art as being suitable for the filtration of fine particle size contaminants are comprised of fiber-fiber or fiber-particulate mixtures formed dynamically into sheet by vacuum felting from an aqueous slurry and then subsequently drying the finished sheet. In those fibrous filter media that depend upon mechanical straining to hold back particulate contaminants, it is necessary that the pore size of the filter medium be smaller than the particle size of the contaminant to be removed from the fluid. For removal of fine, submicronic contaminant particles by mechanical straining, the filter media need have correspondingly fine pores. Since the pore size of such a sheet is determined predominantly by the size and morphology of the materials used to form the sheet, it is necessary that one or more of the component materials be of a very small size, such as small diameter fibers. See, for example, any of Pall U.S. Pat. Nos. 3,158,532; 3,238,056; 3,246,767; 3,353,682 or 3,573,158.

As the size of the contaminants sought to be removed by filtration decreases, especially into the submicron range, the difficulty and expense of providing suitably dimensioned fiber structures for optimum filtration by mechanical straining increases. Accordingly, there is considerable interest in the use of fine particulates such as diatomaceous earth.

However, for such materials it is necessary to provide a matrix in order to present a coherent handleable structure for commerce and industry. Thus, at least one of the component materials in the sheet is a long, self-bonding structural fiber, to give the sheet sufficient structural integrity in both the wet "as formed" and in the final dried condition, to allow handling during processing and suitability for the intended end use. Unrefined cellulose fibers such as wood pulp, cotton, cellulose acetate or rayon are commonly used. These fibers are typically relatively large, with commercially available diameters in the range of six to sixty micrometers. Wood pulp, most often used because of its low relative cost, has fiber diameters ranging from fifteen to twenty-five micrometers, and fiber lengths of about 0.85 to about 6.5 mm.

Filter media sheets are conveniently formed by vacuum felting from an aqueous slurry of the component material. The vacuum felting is performed on a foraminous surface, normally a woven wire mesh which, in practice, may vary from 50 mesh to 200 mesh, with mesh openings ranging from 280 micrometers to 70 micrometers respectively. Finer meshes are unsuitable because of clogging problems and/or structural inadequacy.

The size of the openings in the foraminous vacuum felting surface, and the pore size of the cellulose fiber matrix of the formed sheet, are quite large in comparison to some or all of the dimensions of the fine fiber or particulate components required to produce the desired submicronic filter media sheet. Retention of such fine components during the vacuum formation of the filter media sheet is difficult, and imposes severe constraints on the choice of such materials, the specific details of the process utilized to form the filter media sheet, and, most important, upon the level of filtration performance that may be attained. Fine fibers, whose length may be large in comparison to their diameter, present less of a problem and tend to be retained reasonably well. Fine particulates, on the other hand, tend to show very poor retention during sheet formation.

Flocculation with polymeric retention aids, or coagulation has been used as a means of improving retention of fine particulates, in effecting the grouping of particles to offer an effective large dimension. However, filter sheet prepared from a well-flocculated slurry will have a broad particle size distribution, with small pores occurring inside the flocs, and large pores occurring between the flocs. The existence of these larger pores will limit the ability of the filter media sheet to remove fine contaminants. The use of flocculation to achieve high retention in filter media is therefore somewhat counterproductive.

It is, of course, possible to apply hydrodynamic shear forces, breaking up the flocs, and further charge modify until the system assumes a stable disperse form. This does achieve a relatively uniform sheet of narrow pore size distribution. However, the retention of the particulates in such a system is very low, leading to concomitant reduction of filtration efficiency.

In addition to controlling the dispersion characteristics (and therefore the porosity of the sheet) and providing wet strength, charge modifiers are employed to control the zeta potential of the sheet constituents and maximize performance in the electrokinetic capture of small charged contaminants. In practice, cationic charge modifiers are employed since most naturally occurring contaminant surfaces are anionic at fluid pH of practical interest. Thus, a melamine-formaldehyde cationic colloid is disclosed for filter sheets in U.S. Pat. Nos. 4,007,113 and 4,007,114.

The use of such filter systems with biological fluids poses special problems, among them the possibility of introducing to the fluid impurities resulting from loss of or a breakdown in filter elements. While certain levels of particular impurities may be tolerable in some instances, organic extractables pose especially sensitive problems in the filtration of foods and pharmaceutical products. In filter systems composed of cellulose fiber as a matrix for particulate filter aids modified with an organic cationic resin, organic extractables are naturally primarily traceable to the resin. Selection of the charge modifying resin can alleviate the problem, even under relatively stringent conditions of use including sanitization and sterilizable procedures. Even in the absence of meaningful levels of extractables, however, many resins of choice are subject to discoloration in use, tending to limit their marketability for food and drugs.

Further, even low levels of certain organic extractables are unacceptable in some systems, and accordingly it is desirable for this reason and that of aesthetics to wholly remove the organic charge modifier resin from the filter construction. At the same time, it is necessary for the removal of submicron negatively charged contaminants to retain the positive charge potential afforded by a charge modifying resin.

It is accordingly an object of the present invention to provide charge modified filter media sheets of enhanced filtration performance, especially for the removal of submicron contaminants from aqueous systems at high efficiency.

Another object is to provide charge modified filter media characterized by low organic extractables over a wide range of filtration conditions.

A still further object is the provision of filter media effective across the spectrum of biological liquids and, particularly, ingestables such as foods and drugs.

These and other objects are achieved in the practice of the present invention as described hereinafter.

GENERAL DESCRIPTION OF THE INVENTION

In accordance with the present invention, charge modified filter media sheets are prepared utilizing an inorganic charge modifier constituted by cationic colloidal silica. The filter media sheet, preferably formed by vacuum felting of a cationically disperse aqueous slurry comprising beaten cellulose fibers and fine particulate shows a uniform, high porosity, and fine pore size structure with excellent filtration and flow characteristics. Thus, the sheets comprise cellulose fiber as a matrix, and particulate filter aid, the surfaces of at least one of which have been modified with cationic colloidal silica. Those sheets are free of extractables, such as formaldehyde or amines originating with organic resinous charge modifiers, and are free of discoloration, such that the sheets are usable under any sterilizing conditions and may be employed safely and effectively with potables or ingestables such as food or drugs.

The cationic colloidal silica is an aqueous dispersion of positively charged colloidal particles consisting of a dense silica core coated with a positively charged polyvalent metal-oxygen compound typically stabilized with a counterion. Illustrative such materials are disclosed in U.S. Pat. No. 3,007,878 incorporated herein by reference. Other surface modified cationic colloidal silica materials are known for insolubilization of enzymes, for example as shown in U.S. Pat. No. 3,796,634 but are characterized by the presence of organic modifying resins and hence are contraindicated for use in conjunction with the present invention.

While the principal requirement for this component of the filter system is that it functions as a charge modifier and dispersion agent, it should also be able to interact with the matrix to provide strong bonding as by cross-linking. U.S. Pat. Nos. 3,775,141 and 3,785,838 disclose refractory compositions comprising inorganic fibers bonded with cationic colloidal silica into integral structures which may also comprise a proportion of inorganic filler such as perlite. It is surprising then, in that the bonding of organic to inorganic materials is more difficult to achieve, to find that strong bonds are achieved with cellulose fiber upon curing with cationic colloid silica. However, the bonding once achieved is relatively more inert to its surrounding environment, and loss of the material by hydrolytic or solvolytic action, believed to be among the causes of impurities or extractables generated in other systems, is obviated.

In preferred embodiments of the invention, relatively high loadings of fine particulates such as diatomaceous earth or perlite, to 50-70 percent of more by weight of the sheet, are employed. Without wishing to be bound by an essentially hypothetical elucidation, it is believed that surface modification of these materials with cationic silica colloid, particularly at these high loadings, contributes to the integrity of the overall structure, and may be attributable to the formation of some siliceous, or inorganic interbondings, interengaging the relatively low level (10-20%) of cellulose fibers comprising the total sheet weight in such embodiments, with the particulates by way of the cross-linking action of the active hydroxyl sites provided by the colloidal silica.

BRIEF DESCRIPTION OF THE DRAWINGS

The present invention is further illustrated by the accompanying drawings, in which.

DETAILED DESCRIPTION OF THE INVENTION

The filter media sheets of the invention are prepared from cationically modified filter elements, usually in the form of a cationically disperse aqueous slurry comprising cellulose fiber and optimized levels of fine particulate such as diatomaceous earth or perlite. The filter elements may be cationically modified in the slurry and the sheet prepared dynamically by vacuum felting, and drying, or the filter elements may be pretreated and formed into sheet media. A special feature of the invention is the provision of filter media sheet in which the level of particulate retained is enhanced as compared to sheet prepared conventionally.

The state of refinement of a wood pulp fiber is determined by means of a "freeness" test in which measurement as the flow rate through a forming pad of the fibers on a standard screen is determined, most commonly utilizing the "Canadian Standard Freeness Tester". In this method, the quantity which is measured is the volume of water (expressed in ml.) which overflows from a receiver containing an orifice outlet at the bottom. The Canadian Standard Freeness measurements are employed in the present specification. Coarse unbeaten wood pulp fibers produce high drainage rates into the receiver from the screen resulting in large overflow volumes, and hence record a high freeness. Typical wood pulps show Canadian Standard Freeness values ranging from +400 ml. to +800 ml. In paper or filter media manufacture, such pulps may be subject to mechanical refining processes such as beating, which tends to cut and/or fibrillate the cellulose fibers. Such beaten fibers exhibit slower drainage rates, and, therefore, lower freeness.

In accordance with the present invention, such beaten pulp is preferably employed in the self-bonding matrix for the filter media. The Canadian Standard Freeness of the pulp system will vary with pulp selection, and may be reflective of varying states of subdivision or refinement, as where different pulps or differently beaten pulps are combined for sheet formation, but the beaten pulp will be employed to provide a composite or average value ordinarily ranging from 100 to 600 ml., with lower values e.g., 200–300 ml. or less being preferred for higher solids retention.

The wood pulp may comprise as little as 10 percent by weight with up to 20 to 30 percent, by weight of the total, being preferred to provide filter media sheet with structural characteristics suitable for industrial filtration applications.

Performance is enhanced by maximizing the amount of fine particulate in the filter media sheet. While as little as 10 percent of a fine particulate will result in noticeable improvement in filtration performance of either type of media, optimum performance is achieved by utilizing the maximum amount of fine particulate. For industrial filtration, structural characteristics suggest a practicable maximum of about 70 percent by weight. Of course, for less demanding applications, somewhat higher levels will be possible. Generally, levels of 50–70 percent by weight are employed.

There are various types of fine anionic particulates that are suitable for the intended purpose, including diatomaceous earth, perlite, talc, silica gel, activated carbon, molecular sieves, clay, etc. Functionally, the fine particulate should have a specific surface area in excess of one square meter/gram and/or particle diameters of less than 10 microns. In a broad sense, any fine particulate may be suitable (such as J. M. Filter Cel, Standard Super Cel, Celite 512, Hydro Super Cel, Speed Plus and Speedflow; Dicalite 215 and Dicalite 416 and Dicalite 436) and may be evaluated by techniques well-known to the art. Siliceous materials are preferred, and from the standpoint of size, morphology, cost, fluid compatibility and general performance characteristics, the finer grades of diatomaceous earth and perlite filter aids exhibiting a mean particle size of less than 5 microns are most preferred. In many cases, mixtures of more than one type of fine particulate such as diatomaceous earth/perlite for example, in proportion by weight of from about 80/20 to 20/80 give better filtration performance or better cost/performance characteristics than that achieved by the use of any single type by itself. Similarly, mixtures in all proporations of relatively coarse and fine particulates, e.g., 50/50 parts by weight of 10 and 5 micron diameter particulates may be used.

Suitable cationic colloidal silica materials include those of U.S. Pat. Nos. 3,007,878; 3,252,917; 3,620,978; 3,719,607; and 3,956,171 all incorporated by reference. These are aqueous dispersions of positively charged colloidal particles consisting of a dense silica core coated with a positively charged polyvalent metal-oxygen compound, e.g., of the class consisting of metal oxides, metal hydroxides and hydrated metal oxides of metals having a valence of 3 or 4, preferably aluminum and titanium. Most preferably, the dispersion is acidic, and the coating is of polymeric alumina species. Typically, the mole ratio of aluminum to silica on the surface is about 1:1, and the dispersion (which has been commercially available as Ludox Positive Sol 130M, from E. I. duPont de Nemours & Co.) is stabilized with a counterion, as described in the aforesaid U.S. Pat. No. 3,007,878. The dispersion has been supplied at 30% solids, stabilized with chloride ion (1.4%, as NaCl) for use in the pH range 3.5 to 5.5.

The colloidal particles exhibit a surface area of about 150–225 $m^2/g$ by nitrogen adsorption, a particle diameter of about 15–16 mu, and a molecular weight of about 5 to 18 million by light scattering.

In its preferred form, the characteristics of the silica aquasol are further modified to higher levels of polymeric alumina species calculated as alumina from 13 to 15% or more, in the stable range based upon the colloidal solids. The coating, or overcoating, may be achieved by simply treating with an appropriate aluminum compound, e.g., basic aluminum chloride, as described in U.S. Pat. No. 3,007,878, or another source of polybasic aluminum cations. The alumina in such systems exists as a surface coating and, to the extent it exceeds the available surface area, as free alumina in solution. The free alumina may, of course, also serve as a coating for virgin filter elements, e.g., particulate present and systems so prepared offer improved resistance to autoclaving and hot water flushing conditions together with added wet strength. Where desired, the resulting colloidal dispersion may be, and customarily is treated to remove excessive electrolyte, as by dialysis, in order to achieve storage stability. Filter sheets prepared with the preferred cationic colloidal silica exhibit uniformly acceptable sterilization stability under stringent conditions, e.g., autoclaving at 15 psi, 121° C. for 1 hour.

In paper production, where cationic charge modifiers are sometimes used, the objective is reduction of charge to approximately the isoelectric point to maximize efficiency in interfelting of fiber. For filtration, maximum charge is desired to enhance removal of charged particles by electrokinetic mechanisms. In the present case the surface charge of at least one of the negatively charged filter elements, i.e., cellulose and particulate is reduced to render the surface less electronegative and optionally (and preferably) reversed by the deposition of sufficient cationic charge modifier to render the surface electropositive, to provide at least certain electropositive regions or sites within the filter sheet. In order to accomplish charge reversal, of course, one proceeds through the isoelectric point, and then positive charge buildup is accomplished to the maximum practical level.

The amount of charge modifier employed in the present invention is thus preferably that sufficient to at least provide a cationically disperse system, i.e., a system in which no visible flocculation occurs at ambient conditions in the absence of applied hydrodynamic shear forces. The system therefore comprises essentially discrete fiber/particulate elements exhibiting a positive charge or zeta potential relatively uniformly or homogeneously distributed in and throughout the aqueous medium. The specific level will, of course, vary with the system and the modifier selected but will be readily determined by one skilled in the art. For example, the inflection point on a plot of particulate retention vs. amount of charge modifier approximates the minimum level for better performance. Thus a 5–6 percent level is appropriate for cationic colloidal silica applied during sheet formation, although lower amounts, e.g., 3–4 percent may be sufficient where the filter elements are precoated. Although additional modifier may be employed to advantage where desired, this level represents the best balance on a cost/performance basis. Premodified filter elements e.g., cellulose fiber and particulate precoated with charge modifier may of course be incorporated in any manner into filter sheets with similar results, and where a cationically disperse slurry is not employed, charge modification will be commensurately reduced by control of modifier levels.

The charge modification effected is demonstrable in measurements of surface zeta potential, and in improved filtration efficiency for negatively charged particles in liquid systems.

The slurry of pulp and particulates is formed in any suitable manner. The sequence of adding these components to water to form the initial slurry appears to be relatively unimportant. The consistency of the slurry will represent the highest possible for a practical suspension of the components, usually about 4 percent. The system is subjected to hydrodynamic shear forces as by a bladed mixer, and the charge modifier is then added to the slurry.

The shear level is not critical i.e., any otherwise suitable shear rate or shear stress may be employed having regard for available equipment, preferred processing times etc. but is selected and employed simply to break up the flocs and maintain the system in a dispersed condition during treatment. Of course, upon the formation of a cationically disperse slurry, the system is free of floc formation even in the absence of applied shear.

After charge modification, the slurry is diluted with additional water to the proper consistency required for vacuum felting sheet formation, ordinarily 0.5 to 2½ percent, depending upon the type of equipment used to form the sheet, in a manner known to the artisan. The slurry is formed into a sheet and oven dried in standard manner. The performance of the sheet is related to the drying parameters and optimized conditions may reflect energy considerations or desired thermal history consistent with minimization of unnecessary exposure to elevated temperatures, especially as the decomposition or scorch point for the system is approached.

In accordance with a preferred embodiment of the invention, filter media sheets are formed from filter elements, i.e., particular and a self-bonding matrix of cellulose pulp at least one of which is charge modified, the pulp being a system incorporating beaten pulp to provide a Canadian Standard Freeness of up to 600 ml., preferably less than 300 ml. e.g., 100–200 ml. the charge modifier consisting of cationic silica comprising at least 20% surface alumina and being applied in a proportion to reduce electronegativity of the surface, preferably to achieve charge reversal beyond the isoelectric point, e.g., to an add-on level of about 6% by weight. Filter media sheets so prepared may be autoclaved, hot water flushed or otherwise treated at elevated temperature to sanitize or sterilize the structure. In addition to having special utility for the filtration of biological liquids, these sheets also may be employed for filtration without flush out delay, as ions present in the structure have been removed during the sanitization or sterilization procedure.

Figure 1:
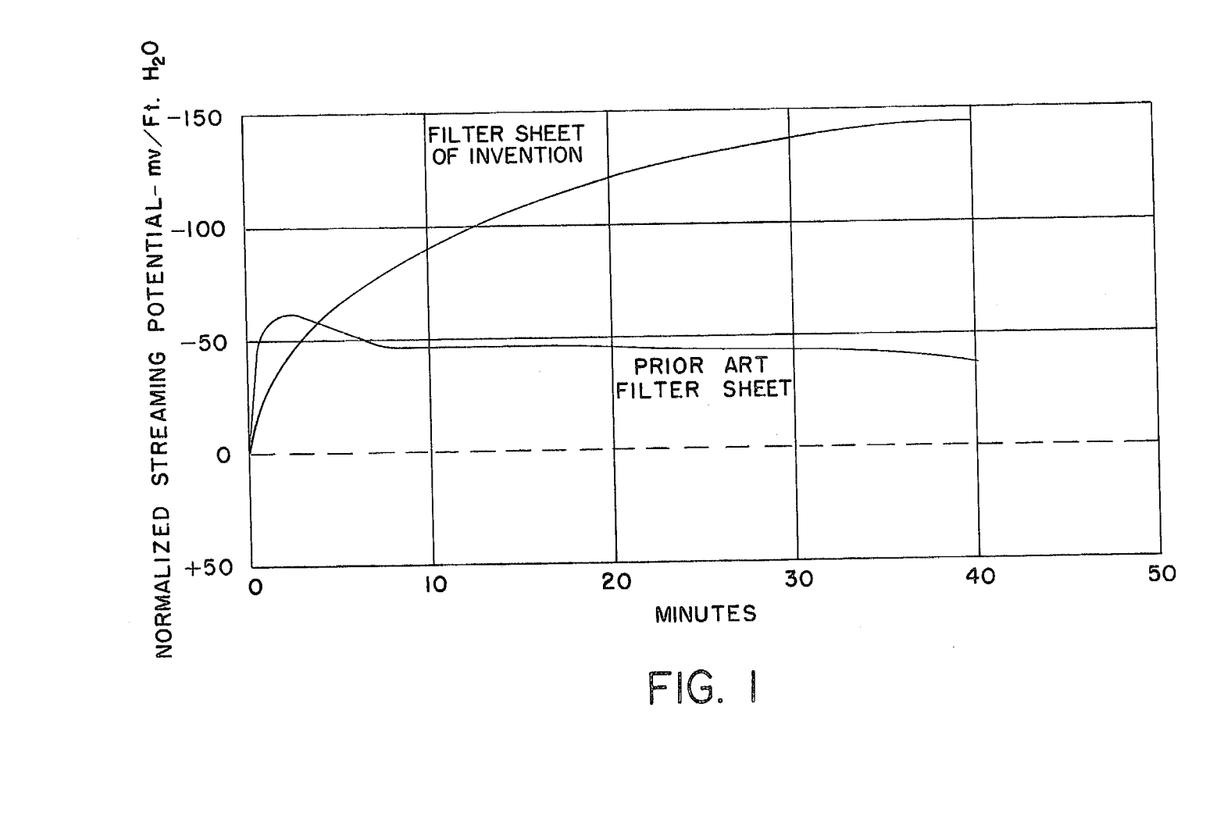
FIG. 1 is a graph of normalized streaming potential vs. time, comparing equilibrium flush out curves for a prior art filter sheet, and a filter sheet manufactured in accordance with the invention.
Figure 2:
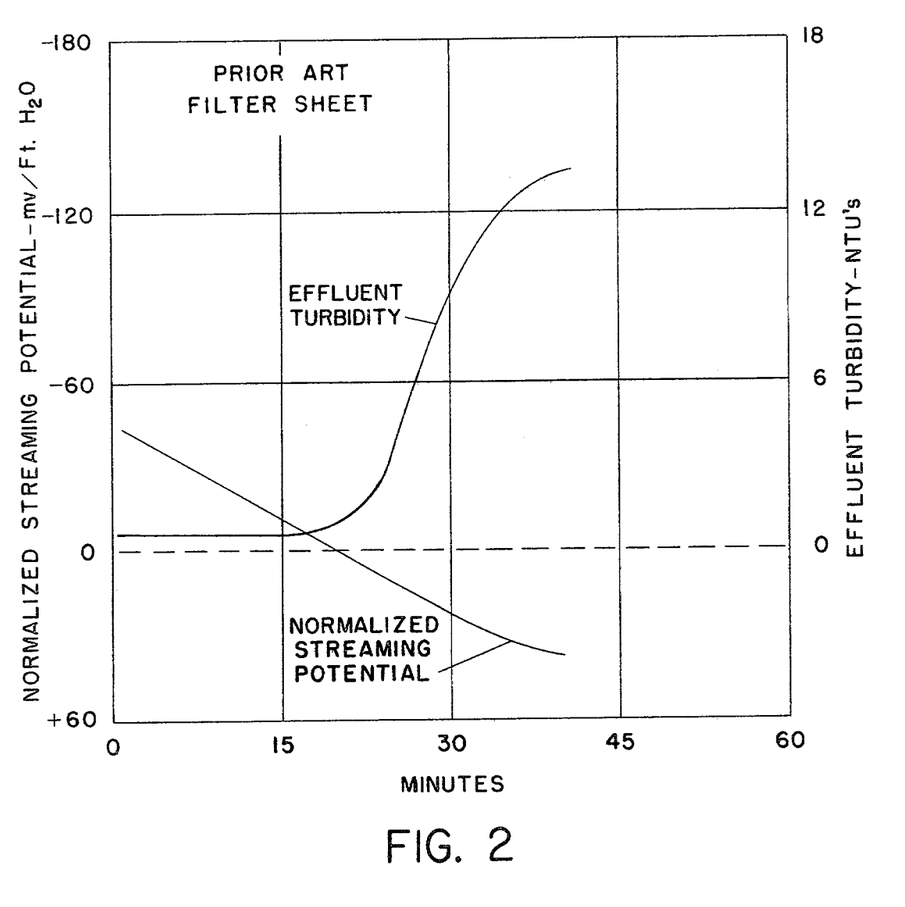
FIGS. 2 and 3 are graphs of normalized streaming potential and effluent turbidity vs. time, comparing monodisperse latex contaminant challenge tests for a prior art filter sheet, and a filter sheet manufactured in accordance with the invention.
Figure 3:
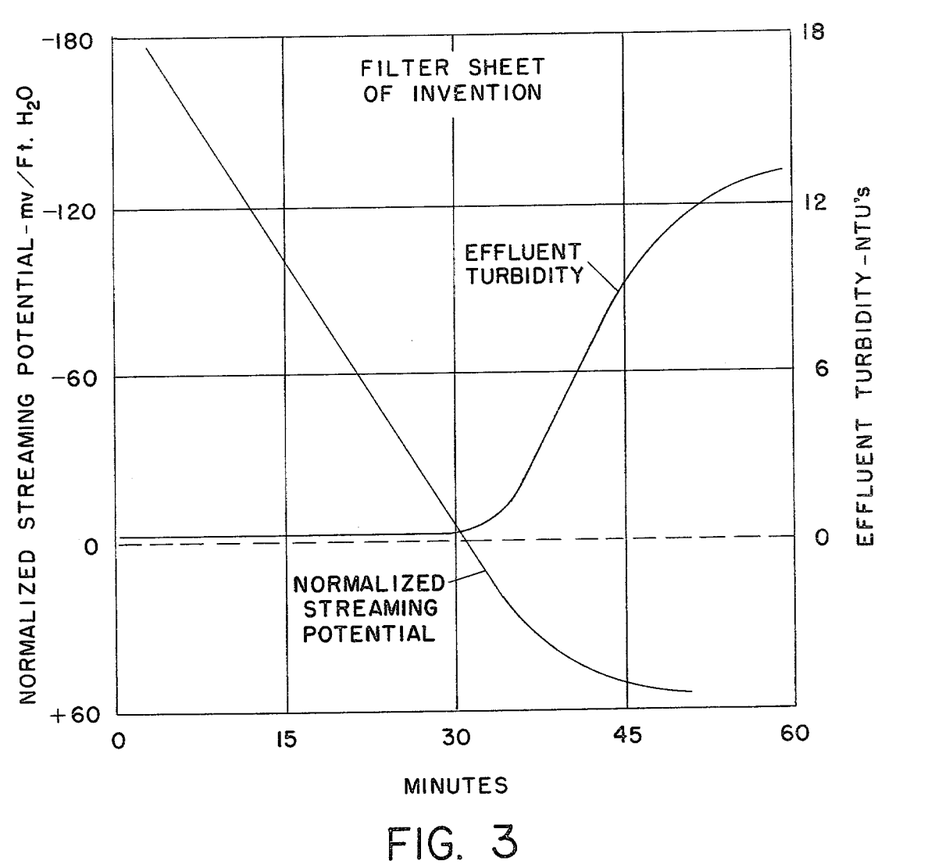

The performance benefits of the cationic colloidal silica may be seen dramatically illustrated in the drawings, representing the results of testing conducted as described in Example V. The cationic colloid silica of the invention retains high charge and contaminant removal capacity and has longer effective life than the melamine-formaldehyde cationic colloid of U.S. Pat. No. 4,007,113.

The filter media sheets may be subjected to standardized testing reflecting performance in use, represented herein by the following:

Filtration Efficiency Test

In this test, contaminated fluid of a specified turbidity as drawn through the test filter media by a constant vacuum under standard conditions, effluent turbidity measured (using a Hach model 2100A Turbidimeter) and expressed as percent filtration efficiency when compared to the inlet turbidity, calculated as $$\text{Efficiency} = \frac{\text{Turbidity In} - \text{Turbidity Out}}{\text{Turbidity In}}.$$

Test contaminant is Hyplar (produced by Grumbacher) a polydisperse acrylic latex produced by emulsion polymerization and comprising colloidal polymer particles ranging from 0.05 to 1.0 micron. Contaminant level is 25–200 NTU (Nephalometric Turbidity Units) is distilled water, at pH 6.5–7.0. Filter sheet is cut into 57 mm dia. discs, and then placed in a Millipore 47 mm vacuum filter holder. 100 ml. of the prepared contaminant dispersion is then filtered through the disc using a 23 in. Hg vacuum.

Membrane Protection Test

In this test, contaminated fluid is pumped under standard conditions through test filter media and a membrane in series at a constant flow rate, and differential pressure with time recorded. The time or total volume of flow passed at a defined pressure increase is a measure of the life of the prefilter, and interrelates satisfactorily with performance in use. Typically, a 47 mm. 0.22 micron membrane is employed at a flow rate of 225 ml./min. Test contaminant is the same Hyplar polydisperse acrylic latex referred to above. Contaminant level is 5–50 NTU (Hach Turbidimeter, Model 2100A). The test is continued until the differential pressure across either the membrane or the test filter paid exceeds 5–10 psid. Membrane protection times of less than a few minutes indicates no practically useful effect.

Oil Flow Test

As a measure of the porosity of the filter media sheets, 100 ssu oil is pumped through the sample sheet until a differential pressure drop of 5 psid is attained, at which point the flow rate (ml./min.) is recorded.

Normalized Streaming Potential

The measurement of streaming potential is a conventional means of determining zeta potential i.e., the electric potential excess of the surface, and the surrounding fluid to the hydrodynamic shear plane, over the bulk potential of the fluid. In the present test, streaming potential values are determined, and normalized for differing pressure drop in the media being tested, expressing the results in units of millivolts per foot of water. The filter media is evaluated by flushing out the filter media with water until the measured streaming potential achieves a relatively stable maximum value. At this point, the filter media has ceased to contribute any significant ionic species to the water, i.e., the inlet resistivity equals the outlet resistivity.

The filter media test cell is based on the design of Oulman, et al. JAWWA 56:915 (1964). It is constructed from Lucite having an effective area of 3.14 square inches (2" diameter) and is equipped with platinum black electrodes. Water and mercury manometers are used to measure the pressure drop across the media being evaluated. Streaming potential values (by convention, of opposite sign to the zeta potential and the surface charge) are measured with a high impedance volt meter. The influent and effluent resistance are monitored with conductivity flow cells (cell constant=0.02/cm) using a resistance bridge.

Upon the attainment of equilibrium streaming potential (i.e., after flush out) contaminant challenge tests may be performed in the same system, using an aqueous dispersion of a single size monodisperse latex, while measuring the 90° light scattering intensity (selected for high relative sensitivity for particle diameters in the 0.1 to 1.0 micrometer range) of the influent and effluent streams, providing a quantitative determination of the filtration efficiency of the filter media. Effluent turbidity is measured using a Moniteck Turbidity Meter. Inlet turbidity is selected to range from 15 to 20 NTU, using a Dow Diagnostics 0.109 micrometer emulsion polymerized polystyrene latex dispersion, and flow rate is maintained relatively constant. The tests above are described in more detail in a paper presented at the 71st Annual AICHE meeting (1978): "Measuring the Electrokinetic Properties of Charged Filter Media", Knight et al.

In the following examples which further illustrate this invention; proportions are by weight, based upon total pulp and particulate, excluding charge modifier.

EXAMPLE I

A series of filter sheets were prepared utilizing Weyerhauser Coho Kraft pulp, beaten to the levels indicated below, and Grefco Dicalite 416 Perlite, having a mean particle size of 3.9 microns.

The charge modifier employed in these runs was a cationic colloidal silica (30% solids) containing about 15% alumina, based upon the weight of colloidal solids (determined by atomic absorption at 309 nanometer with a hollow cathode 1 amp and nitrons oxide-acetylene flame), having a surface area of about 220 $m^2/g$ (nitrogen adsorption) a particle diameter of about 15–16 mu and a molecular weight of about 5–18 million (light scattering).

The total input weight (bone dry basis) of the component materials was 80 grams, exclusive of charge modifier. A constant proportion of pulp (30 percent by weight, or 24 grams) and particulate (70 percent by weight, or 56 grams) was maintained. The components were added to water in a 1 liter polyethylene bucket, with strong agitation, to form an aqueous slurry at two percent consistency, and the charge modifier added. (The system was subjected to hydrohynamic shear by action of a Hei-Dolph stirrer (Polyscience Inc.), having 4 propeller blades, rotating at about 700 rpm on setting 2.) The slurry was subsequently diluted to 0.5 percent consistency and vacuum felted into a sheet ranging from about 0.160 to 0.200 inch thickness (depending upon retention) in a nine inch by twelve inch hand sheet apparatus utilizing a 100 mesh screen. The sheet was subsequently removed, dried in a static oven at 350° F. until constant weight was achieved, and the final weight recorded. Comparison of the final sheet weight with the total input material weight allowed determination of total solids retention in the sheet. Filter sheets were subjected to filtration (membrane protection) and oil flow sheets, as described above. Results are set forth in Table I.

TABLE I

| Sheet No. | Pulp Freeness (CSF) | Charge Modifier Content (Wt. %) | Oil Flow (Ml/Min.) | Membrane Protection Test (25 NTU) | | | |
|---|---|---|---|---|---|---|---|
| | | | | Init. ΔP (PSID) | Time (Min.) | PAD ΔΔP (PSID) | MEMB. ΔΔP (PSID) |
| 1 | 660 | 6 | — | 1.1 | 127 | 0.6 | 5.0 |
| 2 | 660 | 6 | — | 0.9 | 123 | 1.0 | 5.0 |
| 3 | 660 | 0 | 135 | 0.8 | 14 | 1.2 | 5.0 |
| 4 | 500 | 6 | — | 1.5 | 110 | 10.0 | 0.9 |
| 5 | 500 | 6 | — | 1.2 | 115 | 10.0 | 0.5 |
| 6 | 520 | 0 | 67 | 1.0 | 0 | 1.5 | 5.0 |
| 7 | 350 | 6 | — | 1.5 | 73 | 10.0 | 0.8 |
| 8 | 350 | 6 | — | 1.9 | 72 | 10.0 | 0.3 |
| 9 | 400 | 0 | 111 | 0.3 | 5 | 1.0 | 5.0 |
| 10 | 258 | 6 | — | 1.6 | 50 | 10.0 | 0.4 |
| 11 | 258 | 6 | — | 1.8 | 69 | 10.0 | 0.4 |
| 12 | 320 | 0 | 98 | 1.0 | 4.0 | 1.0 | 5.0 |
| 13 | 167 | 6 | — | 2.1 | 48 | 10.0 | 0.5 |
| 14 | 167 | 6 | — | 2.2 | 70 | 10.0 | 0.5 |
| 15 | 200 | 0 | 58 | 1.0 | 1.0 | 1.0 | 5.0 |
| 16 | 100 | 6 | — | 2.8 | 35 | 10.0 | 0.2 |
| 17 | 100 | 6 | — | 2.8 | 48 | 10.0 | 0.3 |
| 18 | 110 | 0 | NOT TESTED | → | → | → | |

As will be seen from the above reported testing, samples which were not charge modified evidenced essentially no membrane protection. Failure in the systems of lowest freeness was by pad plugging, with little increase in membrane pressure drop.

EXAMPLE II

Runs were conducted in the manner of Example I, employing as the particulate Grefco Perlite 426, having a mean particle size of 4.2 microns, and 436 having a mean particle size of 6.0 microns and a constant (6%) level of Wesol PA, a cationic colloidal silica charge modifier available from Wesolite Corp. Wilmington, Del. (4.0% alumina, 22.5% silica, 30% solids). Results are set forth in Table II.

TABLE II

| Sheet No. | Pulp Freeness (CSF) | Charge Modifier Content (Wt. %) | Membrane Protection Test (50 NTU) | | | |
|---|---|---|---|---|---|---|
| | | | Init. ΔP (PSID) | Time (Min.) | ΔΔPAD P (PSID) | MEMB. ΔΔP (PSID) |
| 19 (436 Perlite) | 185 | 6 | 0.7 | 17.1 | 5.0 | 3.0 |

TABLE II-continued

| Sheet No. | Pulp Freeness (CSF) | Charge Modifier Content (Wt. %) | Membrane Protection Test (50 NTU) | | | |
|---|---|---|---|---|---|---|
| | | | Init. ΔP (PSID) | Time (Min.) | ΔΔPAD P (PSID) | MEMB. ΔΔP (PSID) |
| 20 (426 Perlite) | 130 | 6 | 1.4 | 20.6 | 5.0 | 0.5 |

EXAMPLE III

A. Particulate filter aid was precoated in an aqueous slurry at a 2.5% consistency with the below indicated levels of Wesol PA cationic colloidal silica charge modifier over a contact time of about 15 minutes, isolated, drained and dried at 250° F. for 30 minutes.

The treated particulate filter material was slurried in 100 ml. of water and filtered through a porous fritted glass holder base in a Millipore 47 mm. vacuum filter holder, until a ¼ inch thick cake was formed, and filtration efficiency tests were then performed. Results are set forth in Table III.

EXAMPLE III

C. A preformed sheet comprising a 130 C.S.F. pulp system (30% by weight) and Perlite 416 particulate was impregnated with a 6% by weight solution of Wesol PA cationic colloidal silica charge modifier, dried and cured. In filtration tests, membrane protection time was 5.0 minutes, and failure was by pad plugging at 5 psid.

EXAMPLE IV

A. In the manner of Example III A, mechanically defibered cellulose (Solka floc) was precoated with Wesol PA cationic colloidal silica charge modifier, dried and cured, formed into a filter cake, and tested for filtration efficiency.

TABLE III

| Sample No. | Particulate Type | Charge Modifier Content (Wt. %) | EFFICIENCY TEST | | |
|---|---|---|---|---|---|
| | | | Inlet Turbidity (NTU) | Effluent Turbidity (NTU) | Efficiency (%) |
| 20 | DE 215[1] | 0 | 200 | 50 | 75.0 |
| 21 | DE 215 | 1 | 200 | 15 | 92.5 |
| 22 | DE 215 | 3 | 200 | 1.7 | 99.2 |
| 23 | DE 215 | 6 | 200 | 3.8 | 98.1 |
| 24 | PERLITE 416 | 0 | 200 | 100 | 50.0 |
| 25 | PERLITE 416 | 1 | 200 | 69 | 65.5 |
| 26 | PERLITE 416 | 3 | 200 | 0.96 | 99.5 |
| 27 | PERLITE 416 | 6 | 200 | 5.0 | 97.5 |
| 28 | PERLITE 426 | 0 | 200 | 100 | 50.0 |
| 29 | PERLITE 426 | 1 | 200 | 1.4 | 99.3 |
| 30 | PERLITE 426 | 3 | 200 | 1.7 | 99.2 |
| 31 | PERLITE 426 | 6 | 200 | 8.0 | 96.0 |
| 32 | PERLITE 436 | 0 | 100 | 78.0 | 25.0 |
| 33 | PERLITE 436 | 1 | 100 | 1.4 | 98.6 |
| 34 | PERLITE 4106[2] | 0 | 50 | 45 | 10.0 |
| 35 | PERLITE 4106 | 1 | 50 | 0.8 | 98.4 |
| 36 | PERLITE 4106 | 3 | 50 | 1.1 | 97.8 |
| 37 | PERLITE 4106 | 6 | 50 | 3.5 | 93.0 |

[1]DE 215 is Grefco Dicalite calcined diatomaceous earth, having a mean particle size of 2.7 microns.
[2]Perlite 4106 is Grefco Dicalite perlite having a means particle size of 10 microns.

The improvement in filtration performance with charge modification is dramatic, especially with the larger particulates.

EXAMPLE III

B. An aqueous slurry of the precoated particulate prepared as set forth above is alternatively formed into a filter sheet comprising 30 percent by weight beaten pulp as a matrix, and dried. The pulp system employed exhibited a freeness of 130 C.S.F. Membrane protection and oil flow tests were performed, with results set forth in Table IV.

The results are set forth in Table V, as follows.

TABLE V

| Sample No. | Particulate Type | Charge Modifier Content (Wt. %) | EFFICIENCY TEST | | |
|---|---|---|---|---|---|
| | | | Inlet Turbidity (NTU) | Effluent Turbidity (NTU) | Efficiency (%) |
| 42 | Solka-Floc BW-20 | 0 | 10 | 6.9 | 21.0 |
| 43 | Solka-Floc BW-20 | 1 | 10 | 7.9 | 31.0 |
| 44 | Solka-Floc BW-20 | 3 | 10 | 1.5 | 85.0 |
| 45 | Solka-Floc BW-20 | 6 | 10 | 2.5 | 75.0 |
| 46 | Solka-Floc | 0 | 10 | 5.9 | 41.0 |

TABLE IV

| Sheet No. | Particulate Type | Charge Modifier Pretreat (Wt.%) | Oil Flow (Ml/Min.) | Membrane Protection Test (25 NTU) | | | |
|---|---|---|---|---|---|---|---|
| | | | | Init. ΔP (PSID) | Time (Min.) | PAD ΔΔP (PSID) | MEMB. ΔΔP (PSID) |
| 38 | 416 PERLITE | 0 | 21 | 2.0 | 0 | 0 | 10 |
| 39 | 416 PERLITE | 6 | 32 | 1.7 | 9.0 | 0.3 | 5 |
| 40 | 4106 PERLITE | 0 | 262 | 0.6 | 0 | 0 | 10 |
| 41 | 4106 PERLITE | 6 | 266 | 0.6 | 8.3 | 0 | 5 |

TABLE V-continued

| Sample No. | Particulate Type | Charge Modifier Content (Wt. %) | Inlet Turbidity (NTU) | EFFICIENCY TEST Effluent Turbidity (NTU) | Efficiency (%) |
| --- | --- | --- | --- | --- | --- |
| 47 | BW-200 Solka-Floc BW-200 | 3 | 10 | 2.2 | 78.0 |

EXAMPLE IV

B. A filter sheet was formed from a slurry consisting of 30% untreated cellulose pulp and 70% pretreated defibered cellulose from Example IV A, and tested as described in Example III B, with the results set forth in Table VI, as follows.

TABLE VI

| Sample No. | Particulate Type | Charge Modifier Pretreat (Wt. %) | Membrane Protection (5NTU) | | | |
| --- | --- | --- | --- | --- | --- | --- |
| | | | Init. PAD ΔP (PSID) | Time (Min.) | PAD ΔΔP (PSID) | Memb. ΔΔ(PSID) |
| 48 | Solka-Floc BW-20 | 0 | 0.5 | 1.75 | 0 | 10 |
| 49 | Solka-Floc BW-20 | 1 | 0.3 | 1.75 | 0 | 5 |
| 50 | Solka-Floc BW-20 | 3 | 0.3 | 3.00 | 0 | 10 |
| 51 | Solka-Floc BW-20 | 6 | 0.3 | 10.00 | 0 | 5 |

EXAMPLE V

In this Example, the performance of a prior art melamine-formaldehyde cationic colloid (Parez 607) charge modified filter media sheet (see U.S. Pat. No. 4,007,113) was compared to filter media sheet charge modified with cationic colloidal silica (Wesol PA) in accordance with the invention.

A. Filter media sheets were prepared containing 70% by weight of a cellulose pulp system (C.S.F. 130) and 30% by weight of a 50/50 admixture of diatomaceous earth and perlite and were each formed in identical manner by preparing a cationically disperse aqueous slurry, vacuum felting and oven drying, except that optimized charge modifier levels (7% fo Parez 607, and 6% for Wesol PA) and drying conditions were employed.

Employing test conditions detailed above, normalized streaming potential values were determined over time, and equilibrium flush out curves plotted for the respective filter media, compared in FIG. 1. As will be seen, the prior art (melamine-formaldehyde) media exhibits an anomolous flush-out curve, peaking out very rapidly and then slowly decaying with time. The media sheet prepared in accordance with the invention exhibited an increasingly negative normalized streaming potential which stabilized at a high equilibrium value indicative of a high positive surface charge.

B. The same filter media were then challenged with contaminated liquid (0.109 micron Dow Diagnostics latex dispersion; 5.5 pH), and filtration efficiency and normalized streaming potential plotted against time in FIGS. 2 and 3 comparing respectively the prior art (melamine-formaldehyde cationic colloid) system (FIG. 2) with the cationic colloidal silica modified media of the invention (FIG. 3). The negatively charged latex particles are, initially, essentially quantitatively removed by electrokinetic capture and adsorption. The normalized streaming potential decays linearly from a negative value, through zero, and then asymptotically approaches a positive value. As the streaming potential approaches and passes through zero, the effluent turbidity starts to decay (breakthrough). This increase continues until the effluent turbidity asymptotically approaches the inlet turbidity indicating that all of the latex is passing through the filter media.

The filter media sheet of the invention (FIG. 3) retained its filtration performance significantly longer than that of the prior art filter (FIG. 2).

'Biological liquids' as that term is employed in the specification and claims, is a liquid system which is derived from or amenable to use with living organisms, and ordinarily handled and processed under sanitary or sterile conditions, therefore requiring sanitized or sterilized media for filtration. Included are isotonic solutions for i.m. or i.v. administration, solutions designed for administration per os, as well as solutions for topical use, biological wastes or other body fluids which may comprise filterable bodies such as impurities, e.g., bacteria, viruses or pyrogens which are desirably isolated or separated for examination or disposal by immobilization or fixation upon or entrapment within filter media.

Filter media sheets in accordance with the invention may be employed alone or in combination with other such media to treat pharmaceuticals such as antibiotics, saline solutions, dextrose solutions, vaccines, blood plasma, serums, sterile water or eye washes; beverages, such as cordials, gin, vodka, beer, scotch, whisky, sweet and dry wines, champagne or brandy; cosmetics such as mouthwash, perfume, shampoo, hair tonic, face cream or shaving lotion; food products such as vinegar, vegetable oils, extracts, syrups, fruit juices, make-up water or cooking oils; chemicals such as antiseptics, insecticides, photographic solutions, electroplating solutions, cleaning compounds, solvent purification and lubricating oils; and the like for retention of submicronic particles, removal of bacterial contaminants and resolution of colloidal hazes.

The filter media of this invention are particularly suitable for the removal of pyrogens from biological solutions and especially the removal of the most common pyrogens, endotoxins, particularly from parenteral solutions.

Filter media of the invention were evaluated in this regard using two test procedures.

The first involved the passage of small volumes of test solution (10-50 ml.) through 0.9 $cm^2$ disc filters. The test solution was passed through the filters with the aid of a syringe at a constant flow rate. In large volume experiments usually ten liters of test solution was passed through 3.9 $cm^2$ filter at a flow rate of 3.05 gal/sq.ft./min. (4 ml./$cm^2$/min.). For contamination of the test solutions E. coli LPS obtained from Sigma Chemical Company was used. Limulus Amebocyte Lysate (LAL) was used for endotoxin determination, and the sensitivity for each test solution was found to be 30 pg./ml.

Using the small volume procedure, a number of currently available filters were evaluated for endotoxin removal from 0.9% NaCl. From these results, the filter media of this invention appeared to give the best overall pyrogen removal reducing endotoxin levels to less than the limits of the assay (30 pg./ml.) from small volumes when the concentration of endotoxin ranged from 1,000 to 1,000,000 pg./ml. The present filters also removed endotoxin from a large variety of solutions of different pH and salt concentration used for injection. In all cases, the level of endotoxin was reduced below 100 pg./ml. when the original solution was conatminated with 100,000 pg./ml. of endotoxin. The pH of the test solution was found to influence the efficiency of the present filters. Between pH 7.5 and 8.5 in 0.9% NaCl endotoxin removal begins to exceed 100 pg./ml. However, by using two such filters in series, the level of endotoxin can be reduced to less than 30 pg./ml. in solutions originally contaminated with 1,000,000 pg./ml.

Autoclaving was not found to affect the ability of the present filters to remove endotoxin. The volume of wash solution to remove endotoxin initially present in the filters was found to be from less than 2.6 ml./cm² to no more than 6.4 ml./cm² depending on the nature of the solution.

In the initial large volume experiment, a comparison of flow rate indicated performance of endotoxin removal was not affected at flow rates of from 3-12 gal./sq. ft./min. when the solution was contaminated with 100,000 pg./ml. At endotoxin concentration of 1,000,000 pg./ml., the present filters were capable of reducing the level of endotoxin below 100 pg./ml. This experiment also indicated that the present filter could remove at least 2.5 mg./cm² of endotoxin from 0.9% NaCl pH 7.0. These filters were also found capable of reducing the level of endotoxin below 100 pg./ml. from large volumes of distilled water and 20% Dextrose. At high pH, two such filters were used in series to reduce the endotoxin level to below 100 pg./ml.

Changes in solution pH or salt concentration was not found to result in any large scale release of previously adsorbed endotoxin.

In summary, the present filter media are capable of endotoxin removal from heavily contaminated solutions used for injection. In all solutions below pH 8.5 these filters reduced endotoxin below 30 pg./ml. when originally contaminated with 100 ng. (100,000 pg./ml.) of endotoxin. Solutions containing 1,000 ng./ml. (1,000,000 pg./ml.) endotoxin can be reduced to below 100 pg./ml. by these filters. With two of these filters in series, endotoxin levels can be kept below 30 pg./ml. in most solutions even with pH's exceeding 8.5. The present filter media have greater endotoxin removing ability than comparable filters, e.g., those including cationic melamine-formaldehyde and polyamido-polyamine epichlorodrin as charge modifier on otherwise comparable media, as well as asbestos filters when directly compared under the same experimental conditions.

The present new filters are effective in the removal and retention of lipopolysaccharide (LPS) obtained from a variety of common waterborne bacteria. Both large and small LPS aggregates, including small LPS-containing pieces of bacterial cellular debris are effectively removed by the present filters from supernatants obtained by centrifuging lysed bacterial cells. For this purpose, were used the following bacteria, all isolated from water and identified as:

A Acinetobacter calcoaceticus
B Alcaligenes faecalis
C Citrobacter freundii
D Enterobacter agglomierans
E Flavobacterium capsulatum
F Flavobacterium devorans
G Pseudomonas aeruginosa
H Pseudomonas fluorescens
I Pseudomonas maltophilia
J Zooglea species The method employed involved growing the microorganism for 72 hours at room temperature in soybean casein digest broth. The cells were removed by centrifugation and resuspended in pyrogen-free deionized water wherein the cells were broken by high frequency sound in a sonifier cell disrupter. Large fragments of the cells were removed by centrifugation at 3500 g. for 10 minutes. The supernatants were diluted with pyrogen-free deionized water until a concentration of 10,000 pg./ml. LPS was reached (roughly equivalent to broken cell fragments that may occur in deionized water systems) and then filtered with the present new filters. All filters were autoclaved at 121° C./15 min. prior to use. The results are given in the following Table:

| Species | *Pyrogenic activity broken cell suspension | +Pyrogenic activity after filtration | |
|---|---|---|---|
| | | 100 ml. | 500 ml. |
| A | 20,500 | 110 | 100 |
| B | 10,700 | 50 | 75 |
| C | 9,000 | 55 | 45 |
| D | 12,200 | 105 | 90 |
| E | 14,000 | 125 | 95 |
| F | 12,800 | 85 | 110 |
| G | 17,300 | 120 | 125 |
| H | 18,600 | 110 | 125 |
| I | 8,100 | 75 | 80 |
| J | 9,900 | 80 | 85 |

*Expressed as pg./ml. LPS based on the LAL test and rounded to the nearest 100 pg.
+As determined by the LAL test (Mallinkrodt) with a lower limit of detection of 25 pg./ml. Rounded to the nearest 5 pg.

What is claimed is:

1. A filter media sheet consisting essentially of fine particulate and a self-bonding matrix of cellulose fiber, the surfaces of at least one of which are modified with a sufficient amount of an inorganic cationic colloidal silica to provide a positive zeta potential to the surface of the filter media sheet, wherein the cationic colloidal silica is derived from a dispersion of positively charged colloidal particles having a dense silica core modified with a polyvalent metal-oxygen compound wherein the polyvalent metal is aluminum, and a sufficient amount of the compound is provided to coat the silica to a level of at least 13% by weight of colloidal solids.

2. The filter media sheet of claim 1, wherein the matrix incorporates beaten cellulose fiber to provide a Canadian Standard Freeness of less than 600 ml.

3. The filter media sheet of claim 1, comprising cationic colloidal silica to provide a positive zeta potential to at least one of said fiber and said particulate.

4. The filter media sheet of claim 1, comprising from about 3% to about 6% by weight cationic colloidal silica.

5. The filter media sheet of claim 1, wherein the silica dispersion comprises at least 15% alumina by weight of colloidal solids.

6. The filter media sheet of claim 1, wherein the fine particulate comprises at least 50% by weight of diatomaceous earth.

7. The filter media sheet of claim 1, wherein the fine particulate comprises an admixture of diatomaceous earth and perlite.

8. The filter media sheet of claim 1, wherein the fine particulate exhibits an average particulate dimension of less than about 10 microns.

9. A method for the preparation of filter media sheets adapted for the removal of electronegative submicron contaminants from contaminated liquids comprising:

felting a filter sheet from an aqueous slurry containing a composition consisting essentially of fine particulate and a cellulose pulp system as a self-bonding matrix, the surfaces of at least one of said particulate and said pulp being modified with a sufficient amount of an inorganic cationic colloidal silica to provide a positive zeta potential to the surface of the filter media sheet, wherein the cationic colloidal silica is derived from a dispersion of positively charged colloidal particles having a dense silica core modified with a polyvalent metal-oxygen compound wherein the polyvalent metal is aluminum, and a sufficient amount of the compound is provided to coat the silica to a level of at least 13% by weight of colloidal solids and drying said sheet.

10. The method of claim 9, wherein the pulp system incorporates beaten pulp to provide a Canadian Standard Freeness for the system of 100 to 600 ml.

11. The method of claim 9, wherein the silica dispersion comprises at least 15% alumina by weight of colloidal solids.

12. The method of claim 11, further including the step of sanitizing or sterilizing the sheet.

13. The method fo claim 12, wherein the sheet is autoclaved.

14. The method of claim 12, wherein the sheet is hot water flushed.

* * * * *

UNITED STATES PATENT AND TRADEMARK OFFICE
CERTIFICATE OF CORRECTION

PATENT NO. : 4,305,782
DATED : December 15, 1981
INVENTOR(S) : Eugene A. Ostreicher and Kenneth C. Hou It is certified that error appears in the above—identified patent and that said Letters Patent is hereby corrected as shown below:

On the title page,
the "Related U.S. Application Data" section and Column 1, lines 4 and 5 should read as follows:

--This application is a continuation-in-part of of U.S. Serial No. 027,568, filed April 6, 1979, now abandoned, which is a continuation-in-part of U.S. Serial No. 666,815, filed March 15, 1976, now abandoned--

Signed and Sealed this

Fourth Day of May 1982

[SEAL]

Attest:

GERALD J. MOSSINGHOFF

Attesting Officer

Commissioner of Patents and Trademarks